United States Patent [19]

Swajger

[11] Patent Number: 5,443,471
[45] Date of Patent: Aug. 22, 1995

[54] QUICK RELEASE HANDLE ASSEMBLY

[75] Inventor: Glenn Swajger, Wayne, N.J.

[73] Assignee: Howmedica, Inc., N.Y., N.Y.

[21] Appl. No.: 17,924

[22] Filed: Feb. 16, 1993

[51] Int. Cl.6 ............................................. A61B 17/00
[52] U.S. Cl. ........................................ 606/99; 606/79;
606/86; 403/294; 403/316; 403/324; 623/13;
433/146; 433/147
[58] Field of Search ............... 606/53, 79, 80, 84,
606/85, 86, 99; 623/11, 22, 23; 403/316, 315,
325, 324, 294, DIG. 4; 433/126–129, 146, 147

[56] References Cited

U.S. PATENT DOCUMENTS

| 1,138,465 | 5/1915 | Fegley et al. | 403/325 |
|---|---|---|---|
| 3,280,439 | 10/1966 | McCarthy | 24/211 |
| 4,306,550 | 12/1981 | Forte . | |
| 4,367,971 | 1/1983 | Coren | 403/330 |
| 4,577,367 | 3/1986 | Durand | 16/114 |
| 4,583,270 | 4/1986 | Kenna | 29/80 |
| 4,587,964 | 5/1986 | Walker et al. . | |
| 4,601,289 | 7/1986 | Chiarizzio et al. . | |
| 4,739,750 | 4/1988 | Masse et al. . | |
| 4,765,328 | 8/1988 | Keller et al. . | |
| 4,782,833 | 11/1988 | Einhorn et al. | 606/80 |
| 4,820,154 | 4/1989 | Römhild et al. | 433/128 |
| 4,921,493 | 5/1990 | Webb, Jr. et al. | 606/85 |
| 4,930,932 | 6/1990 | LeVahn | 403/325 |
| 4,940,410 | 7/1990 | Apap et al. | 433/128 |
| 4,985,035 | 1/1991 | Torre | 606/167 |
| 4,990,149 | 2/1991 | Fallin | 606/85 |
| 5,002,581 | 3/1991 | Paxson et al. | 623/18 |
| 5,089,003 | 2/1992 | Fallin et al. | 606/85 |
| 5,135,529 | 8/1992 | Paxson et al. | 606/85 |
| 5,147,408 | 9/1992 | Noble et al. | 623/23 |

Primary Examiner—Stephen C. Pellegrino
Assistant Examiner—Jeffrey A. Schmidt
Attorney, Agent, or Firm—Pennie & Edmonds

[57] ABSTRACT

A handle for use in implanting a prothesis has an elongate body portion and a post-retaining structure at the end of the body portion. The post-retaining portion or structure includes a core member which has a bore formed therein to receive a post connected, for example, to a broach or rasp. The core member also includes a channel formed therein in communication with the bore and a pin movable within the channel between a locked position at the distal end of the channel in communication with the bore and a released position. A spring and a collar are provided where the collar is adapted to slide over the core member, move the pin within the channel and retain the pin in the locked position while the spring is adapted to bias and/or move the collar toward the front end of the core to retain the pin. A movable sleeve fits over the collar and spring and is provided with a shoulder to engage and move the collar to release the pin within the channel.

7 Claims, 5 Drawing Sheets

QUICK RELEASE HANDLE ASSEMBLY

BACKGROUND OF THE INVENTION

The present invention relates generally to surgical instruments used in connection with the implant of prosthetic joints and more particularly to a handle assembly which is used with a broach or rasp to contour the bone where a femoral prosthesis is implanted in a femur.

In the replacement of a hip joint, it is often necessary to replace the natural femoral head with a femoral prosthesis which includes a femoral stem and head. The procedure for implanting the femoral prosthesis usually includes the use of a broach, rasp or trial prothesis for preparing the proximal femoral shaft for the reception of the prosthetic stem. The purpose of the broach or rasp is to contour the medullary canal of the bone to precisely locate and fit the prosthetic stem.

A number of instruments to hold the broach, rasp or trial prothesis have been suggested. U.S. Pat. No. 4,306,550 shows a chuck assembly for engaging a generally cylindrical pilot post. The collar has a traverse slot bisecting it into two portions and a locking member extending across the socket. The locking member engages a slot in the post when the portions of the collar are compressed by axial movement of a knob over the collar.

U.S. Pat. No. 4,583,270 shows a rasp handle having a fixed jaw and a sliding jaw each having semi-cylindrical recesses which together form a cylindrical recess for receiving the shank of a rasp tool. The fixed jaw 22 has an internal semi-circular rib that cooperates with an annular depression on the shank to hold the rasp.

U.S. Pat. No. 4,990,149 discloses a broach handle in which attachment and release is accomplished by a long slender slider bar translating in a longitudinal slot of the handle to register with a recess in the cylindrical post of the broach. U.S. Pat. No. 4,921,493 shows a cutter having a post having ribs which engage a recess in the handle by lateral movement to oppose longitudinal separation and a longitudinally slidable locking pin in the handle to engage a bore in the cutter to oppose lateral movement.

SUMMARY OF THE INVENTION

Accordingly, it is an object of the present invention to provide a broach, rasp or trial prothesis handle which is highly effective in retaining and manipulating a broach or rasp tool which can be quickly and easily released from the handle following such use. It is also an object that the broach, rasp or trial prothesis can be quickly and easily attached to the handle.

In accordance with the present invention, a handle for use in implanting a prothesis has an elongate body portion and a post-retaining structure at the end of the body portion. The post-retaining portion or structure includes a core member which has a bore formed therein to receive a post connected, for example, to a broach or rasp. The post and bore are preferably D-shaped and the post has a notch formed in its flat side. The core member also includes a channel formed therein in communication with the bore and a pin movable within the channel between a locked position at the distal end of the channel in communication with the bore and a released position. The handle further includes means to retain the pin at the end of the channel in communication with the bore and means to release the pin such that it can move within the channel.

Preferably, the channel is formed at an acute angle ($0° < \alpha < 90°$) to the bore and in a direction extending away from the front end of the core member where the post is received. In a further preferred embodiment, a spring and a collar are provided where the collar is adapted to slide over the core member, move the pin within the channel and retain the pin in the locked position while the spring is adapted to bias and/or move the collar toward the front end of the core to retain the pin. A movable sleeve is preferably provided to free the pin within the channel. The sleeve is adapted to interact with the collar to release the pin within the channel. To move the sleeve, a slide lever is preferably interconnected with the handle by a pivot pin. Displacement of the slide lever moves the sleeve to thereby move the collar to thus release the pin within the channel.

BRIEF DESCRIPTION OF THE DRAWINGS

FIG. 4 is an elevational view of the core member at the front end of the broach handle viewed in the direction of line 4—4 of FIG. 2;

DETAILED DESCRIPTION OF THE DRAWINGS

Figure 1:
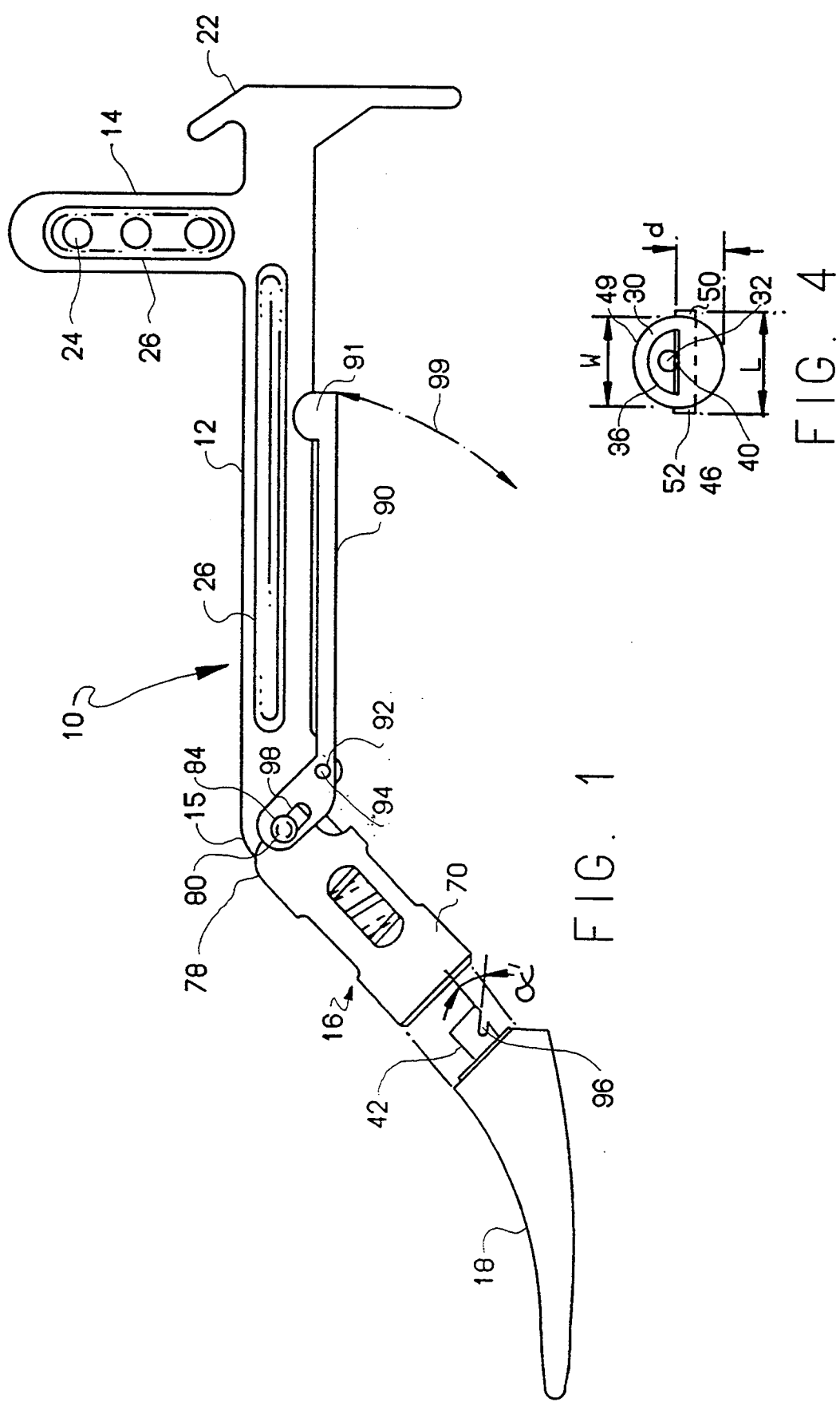
FIG. 1 is a side elevational view of a broach assembly according to the present invention.

Referring more particularly to the drawings, a handle 10 used for the implant of prosthetic joints, for instance such as a broach or rasp handle, has an elongate body portion 12 with a pistol-type grip 14 extending therefrom. Post-retaining portion 16 is provided at the front end 15 of the body portion 12 for locking a post or trunnion 42 of a broach, rasp or artificial prothesis 18 (generally referred to as tool 18) to the handle 10. The end opposite the post retaining portion 16 has a plate 22 adapted either to be hammered against or to facilitate grasping of the handle 10. The handle 10 may be fabricated from stainless steel or other similar material by techniques well-known in the art. The grip 14 as shown in FIG. 1 and the body portion 12, if so desired, may include openings 24 and recessed areas 26 on opposite sides thereof to eliminate unnecessary material from the handle 10 without adversely affecting its overall strength.

Figure 2:
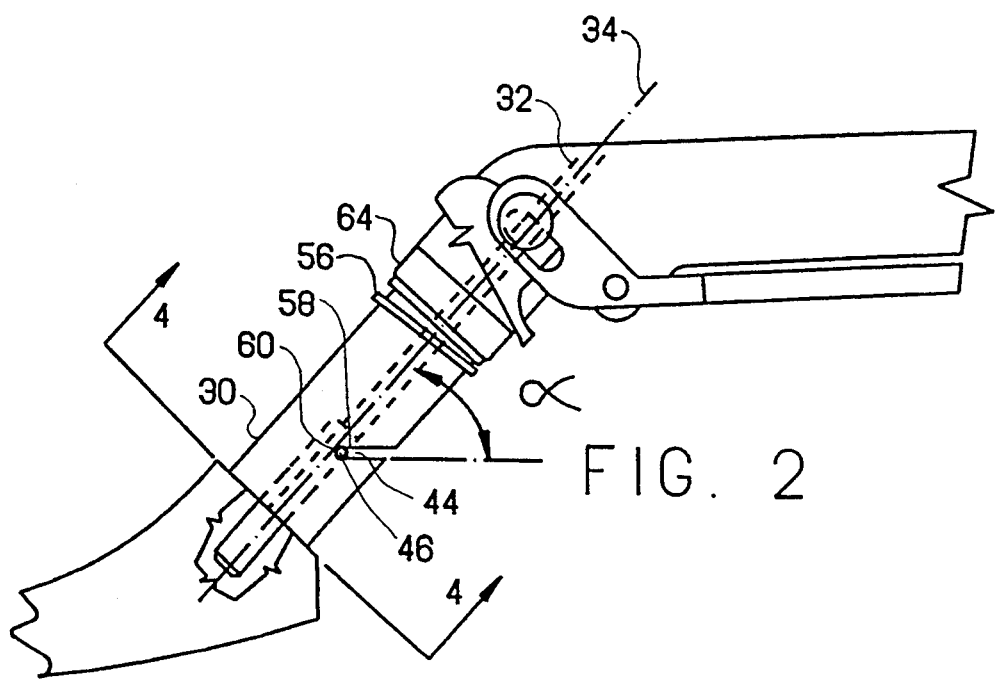
FIG. 2 is a side elevational view similar to FIG. 1 with portions being broken away in order to show interior detail.
Figure 3:
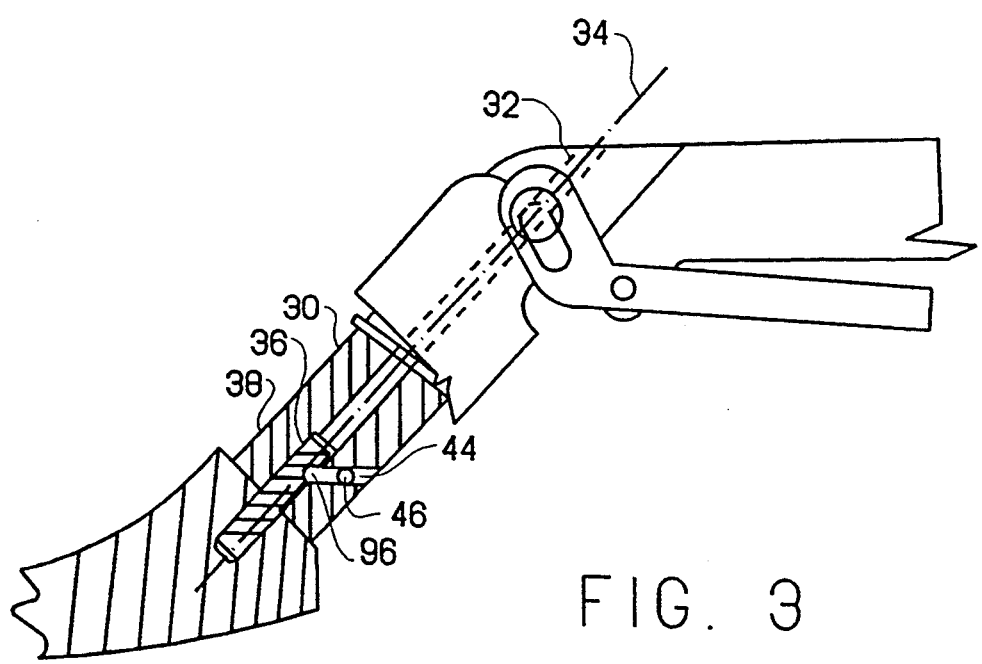
FIG. 3 is a side elevational view similar to FIG. 2 with the handle being in its open broach receiving and releasing position, portions being broken away in order to show interior detail.

As shown in FIGS. 2, 3 and 4, post-retaining portion 16 at the front end 15 of the body portion 12 includes a cylindrical core member 30. A D-shaped bore 36 is formed in the front end 38 of core member 30 along the core member's longitudinal axis 34. The D-shaped bore 36 extends only partially along the longitudinal axis 34 of the core's front end 38 and is configured to receive a D-shaped post or trunnion 42 which is a part of the tool 18. The configuration of the D-shaped bore 36 and cooperating D-shaped post 42 provides the proper orientation of the tool 18 with respect to the handle 10. The D-shaped bore 36 and post 42 also prevent the tool 18 from spinning within the handle 10. While the bore 36 and mating post 42 are illustrated as D-shaped, any cooperating configurations are acceptable., preferably cooperating configurations which provide an orienting function.

Core member 30 may also include an axial bore 32 extending the entire length therethrough along the core's longitudinal axis 34 to eliminate unnecessary material. As illustrated in FIG. 2, the axial bore 32 may communicate with the D-shaped bore 36 such that the flat side 40 of the D-shaped bore 36 is tangent to the axial bore 32.

The core member 30 includes a channel or guide 44 formed in its wall. The channel 44 communicates at its distal end 58 with the flat side 40 of the D-shaped bore 36. Channel 44 forms an acute angle $\alpha$ ($0° < \alpha < 90°$) with the D-shaped bore 35 and extends in a direction away from the front end 38 of the core member 30 as shown in FIGS. 2 and 3. The angle $\alpha$ ranges from $20° < \alpha < 60°$ and preferably is approximately $30°$. The channel 44 retains a movable pin 46 which slides therein. The channel 44 is formed such that when the pin 46 is at the channel end 58, the pin 46 protrudes slightly into D-shaped bore 36 with the depth d of the channel 44 determining how much the pin 46 protrudes into D-shaped bore 36.

The pin 46 is slightly longer in length L than the width W of the channel 44 at its widest location. Due to the circular cross-section of core 30, channel 44 is the widest at the channel end 58 where the pin 46 is shown in FIGS. 2 and 4. In this manner as illustrated in FIG. 4, the pin 46, which is longer than the width of the channel 44, protrudes beyond the channel 44 and the periphery 49 of the core member 30 on both sides 50, 52.

Figure 5:
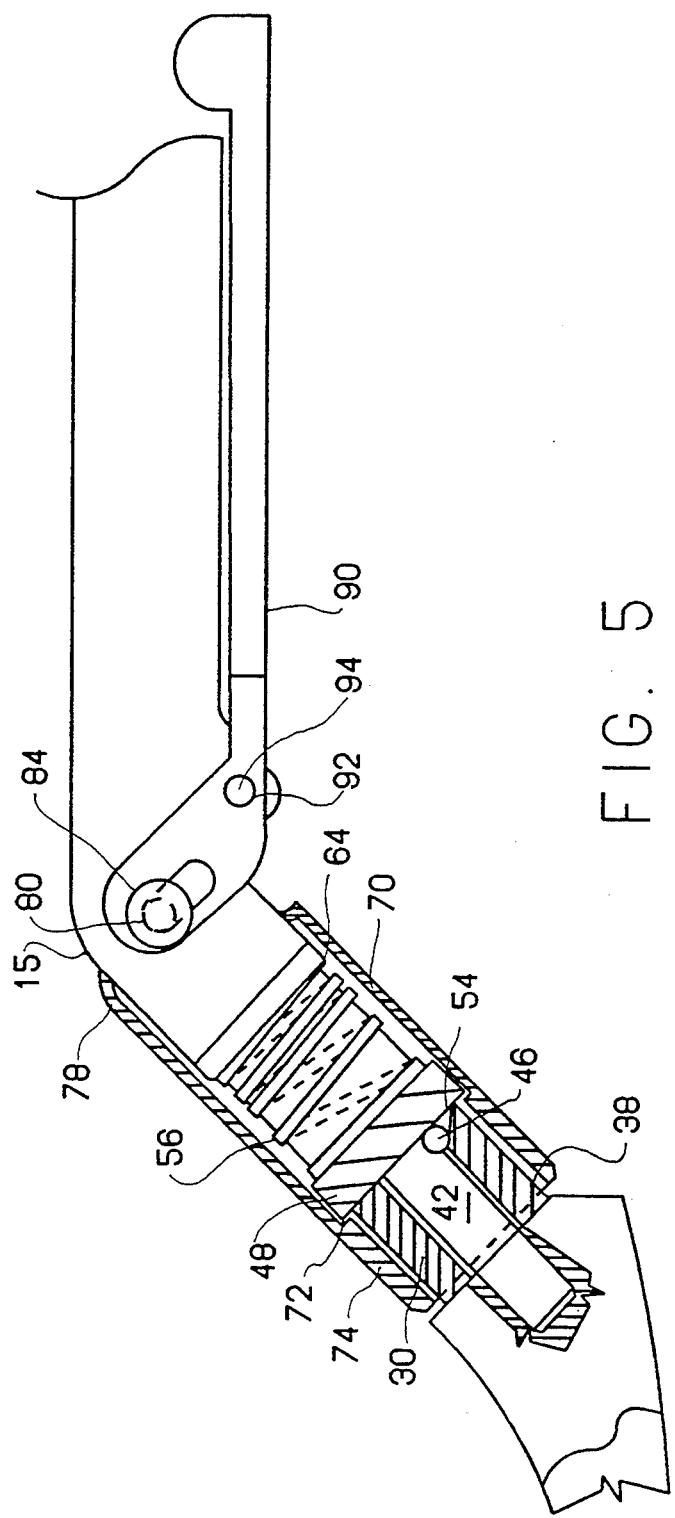
FIG. 5 is a side elevational view similar to FIG. 1 with portions being broken away to show interior detail.

A collar 48, preferably cylindrical in shape, slides over the core member 30 (See FIG. 5). A spring or other biasing means 56 fits over the core member 30 and biases and/or moves the collar 48 toward the front end 38 of the core member 30. The biasing action of spring 56 on the collar 48 moves pin 46 down channel 44 until it reaches channel end 58 where pin 46 rests against the channel end walls of core member 30 and is thus retained. Channel end wall 60 is illustrated in FIG. 2 while a corresponding end wall, not shown, would be formed on the opposite side of core member 30. The spring 56 is positioned and compressed between a shoulder 64 on the core member 30 and the collar 48. The collar 48 and spring 56 can be a single unitary part or two pieces as illustrated in the figures. The pin 46, when located and retained at the channel end 58 by the collar 48, is configured to engage a notch 96 in the post to lock the prosthetic tool 18, such as a broach or rasp, within the handle 10. The notch 96 is preferably formed at an angle $\alpha'$ as shown in FIG. 1 which is preferably substantially the same as angle $\alpha$ shown in FIG. 2.

As shown in FIG. 5, cylindrical sleeve 70 fits over collar 48, spring 56 and core member 30. The sleeve 70 has a shoulder 72 formed at its front end 74 which engages the front edge 54 of the collar 48. The pin 46 is released from the channel end 58 by retracting the sleeve 70 in a direction opposite of the broach 18 to thereby, via shoulder 72, retract the collar 48. By retracting the collar 48, the pin 46 is no longer retained at the channel end 58 and the post 42 and hence the broach 18 is released from the handle 10.

In the embodiment shown in FIG. 5, the front edge 54 of the collar 48 abuts against the pin 46 along portions 50, 52 (FIG. 4) to move and/or retain the pin 46 in the channel 44 at channel end 58. Pin 46 is thus free to move within the channel when it is not retained at the channel end 58 by the collar 48. Nevertheless, the pin 46 is contained and trapped within the channel 44 either by the configuration of the collar 48, sleeve 70, core member 30, or all three in combination.

Figure 7:
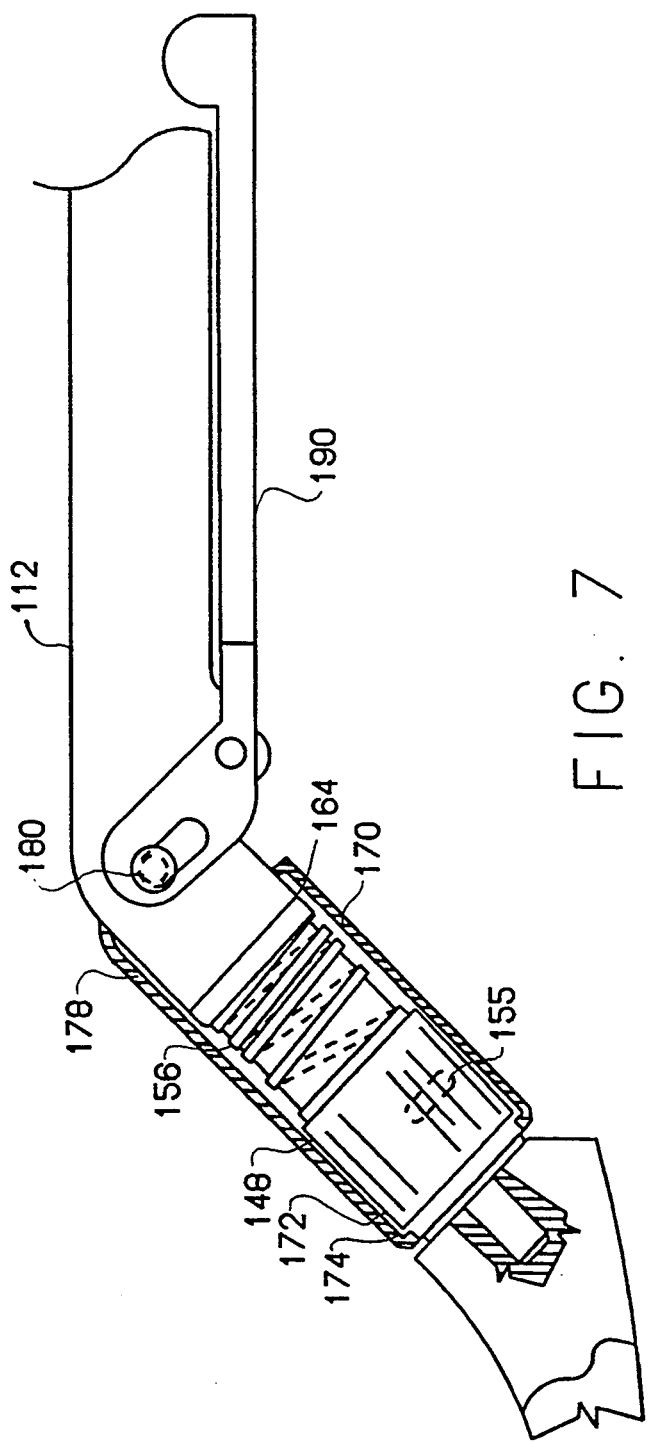
FIG. 7 is a side elevational view of an alternative embodiment of the present invention with portions being broken away to show interior detail.

In an alternative embodiment shown in FIG. 7, raceways or grooves are formed in the interior surface of the collar 148 to retain pin portions 50 and 52 where the pin extends out of the channel 44. Groove 155 is shown in FIG. 7 while a corresponding groove, not shown but labeled 157, is formed opposite groove 155 on the interior wall of the collar 148. The pin portions 50, 52 are retained by and move within the grooves 155, 157 when the collar 148 moves thus causing the pin 46 to be displaced within the channel 44. Unlike the collar 48 of FIG. 5, the collar 148 positively positions the pin 46 within the channel 44 such that the pin 46 cannot freely move within the channel 44 unless the collar 148 also moves.

The sleeve 70 can be retracted as in the embodiment shown in FIG. 1 (and FIG. 5) wherein holes 80, 82 are formed in the back end 78 of the sleeve 70 to receive cam pins 84, 86. A slide lever 90 having elongated slots 98, 99 receives the cam pins 84, 86 to attach the lever 90 to the sleeve 70. The slide lever 90 also contains a hole 92 to retain a lever pin 94. The lever pin 94 connects the lever 90 to the front end 15 of the body portion 12 of the handle 10. The end 91 of the slide lever 90 moves away or adjacent to the body portion 12 as shown by arrow 99 in FIG. 1 by rotating about the lever pin 94. By movement of the lever 90 away from the body portion 12, a force is applied to the sleeve 70 through cam pins 84, 86 to retract the sleeve 70 away from the broach 18. As the sleeve 70 undergoes motion, the cam pins 84, 86 move within elongated slots 98, 99.

Figure 6:
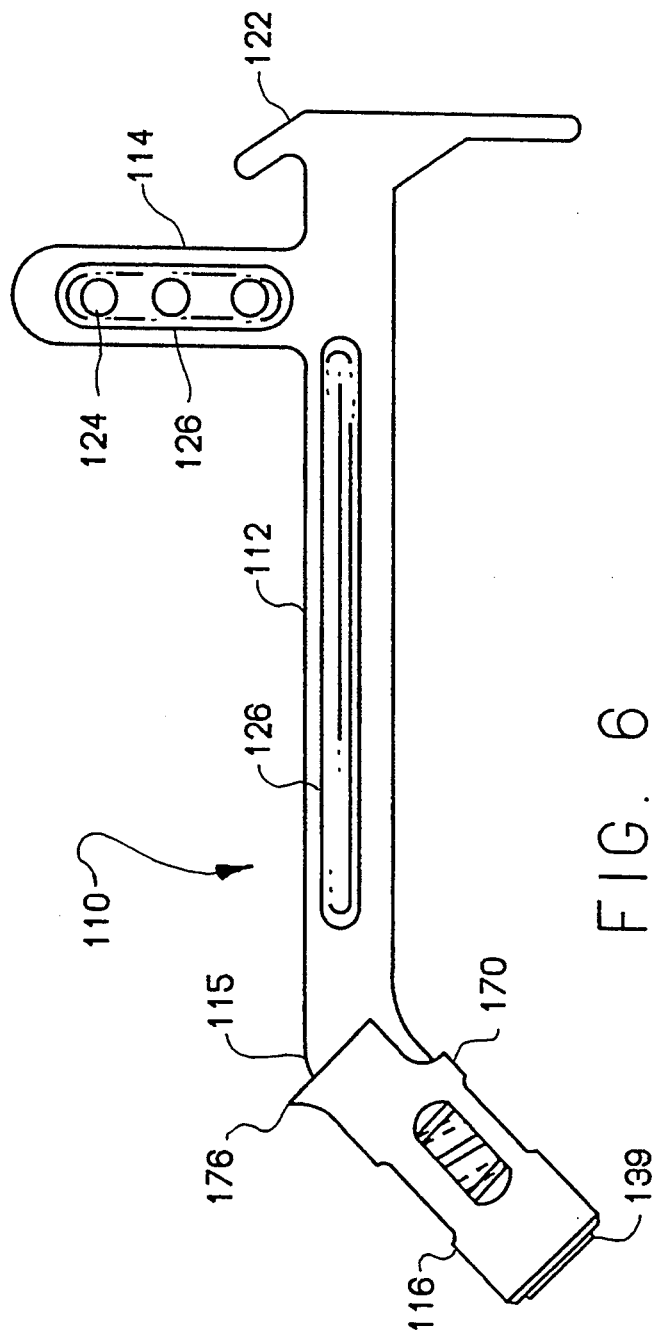
FIG. 6 is a side elevational view of an alternative embodiment of the present invention.

In an alternative embodiment shown in FIG. 6, the sleeve has a gripping portion 176 to hold and retract the sleeve 170 and a lip 139 formed on the core member 30 to act as a stop to retain the sleeve 70 against the bias force of the spring and collar as well as to retain the sleeve 70 on the post-retaining portion 16.

The operation of the handle 10 is more fully described as follows. With a tool 18 assembled, as shown in FIG. 5, the slide lever 90 is in a position adjacent the body portion 12 and the post 42 is retained in a locked position within the core member 30. In this state, the pin 46 is retained at the channel end 58 by the spring 56 acting on the collar 48 causing the pin 46 to protrude within the D-shaped bore 36 and engage the notch 96 in the post 42 to lock the broach 18 within the handle 10. The collar 48 also acts on the sleeve 70 through shoulder 72 to move or in this case bias the sleeve 70 toward the broach 18. The sleeve 70 in this position in turn acts via pins 84, 86 on the slide lever 90 to hold the lever 90 against the body 12.

To release the post 42, the slide lever 90 is moved to a position away from the body portion 12. In this manner, the slide lever 90 moves both the sleeve 70, and via shoulder 72, the collar 48 as well, away from the broach 18. Movement of the collar 48 away from the broach 18 frees the pin 46 within the channel 44 such that the pin 46 is no longer constrained to engage the post-notch 96 such that the tool 18 is released.

Upon release of the slide lever 90, spring 56 resting against shoulder 64 of the core member 30 moves the collar 48 along the core member 30 toward the front end 38. As the collar 48 moves toward the front 38, it abuts against pin portions 50, 52 thereby moving pin 46 down channel 44. End walls 60, 62 stop pin 46 from further movement when pin 46 reaches the channel distal end 58. The pin 46 is retained by the collar 48 and spring 56 at the channel end 58 with the pin 46, and particularly the portions 50, 52, acting as a stop against further movement of the collar 48. In addition, as the collar 48 moves toward the front end 38 it abuts against the sleeve shoulder 72 to thereby move the sleeve 70 toward the broach 18. The movement or bias of the sleeve 70 toward the broach 18 exerts a force on the cam pins 84, 86 which automatically moves the slide lever 90 back against the body portion 12.

To insert and lock tool 18, the post 42 is inserted into the D-shaped bore 36 and tool 18 and handle are simply pushed together to snap the tool in. Alternatively, the slide lever 90 can be moved away from the body portion 12, the post 42 inserted into the D-shaped bore 36 and the slide lever 90 released.

It is to be understood that the above detailed description of the invention is provided by way of example only. Other modifications and variations in the present invention will become apparent to one skilled in the art from an examination of the above specification and accompanying drawings. Therefore, other variations of the present invention may be made which fall within the scope of the appended claims even though such variations were not specifically discussed above.

I claim:

1. Handle assembly for retaining a tool, comprising:
   (a) a first member defining a bore for receiving the tool and a channel disposed at an angle to and communicating with the bore;
   (b) a pin member disposed within the channel and movable from a first locked position extending at least partially into the bore and a second unlocked position;
   (c) a movable collar slidable over the first member;
   (d) means for biasing the collar to retain the pin in communication with the bore;
   (e) a slide lever adapted to slide the sleeve; and
   (f) a pivot pin interconnecting the lever and the first member whereby the lever moves between a position adjacent and a position away from the first member.

2. A tool for reaming a bone canal, comprising:
   a first member having distal and proximal ends;
   a post extending from the proximal end of the first member, said post having a substantially D-shaped cross-section defining a substantially flat side with a notch therein; and
   a quick release handle having,
   a post-receiving member defining a bore for receiving said post and a channel disposed at an acute angle to and communicating with the bore,
   a pin member disposed within the channel and moveable from a first locked position extending at least partially into the bore and into said notch when the post is received in said bore and a second unlocked position, and
   means for retaining the pin member in said first position such that the post received in the bore is retained thereby.

3. Handle assembly for retaining a tool, comprising:
   first member defining a bore for receiving and orienting the tool with the handle and a channel disposed at an angle to and communicating with the bore;
   pin member disposed within the channel and movable from a first locked position extending at least partially into the bore and a second unlocked position;
   means for retaining the pin member in said first position such that the tool received in the bore is retained thereby,
   wherein said means for retaining the pin member comprises a movable collar slidable over the first member and biasing means for biasing the collar to retain the pin in communication with the bore:
   means for releasing the pin from said first position comprising a movable sleeve adapted to move the collar against the biasing means to release the pin; and
   a lever means to move the sleeve,
   the lever means comprises a slide lever adapted to slide the sleeve and a pivot pin interconnecting the lever and the first member whereby the lever moves between a position adjacent and a position away from the first member.

4. A handle comprising an elongate body portion and a post-retaining portion; the retaining portion comprising:
   (a) a core member having a front and back end with a longitudinal bore formed in the front end and a channel in communication with said bore and formed in said core member at an acute angle to the bore;
   (b) a pin movable within the channel between a locked position wherein said pin protrudes and is retained within said bore and a released position wherein the pin is free to move within said channel;
   (c) a movable collar adapted to slide over said core member to move said pin within said channel and retain said pin in said locked position;
   (d) a spring mounted over the core and configured to bias the collar toward the front end of the core and to move said collar against said pin in said locked position;
   (e) a movable sleeve mounted over the collar and adapted to retract said collar to free the pin within the channel;
   (f) a slide lever adapted to slide said sleeve to thereby move said collar toward the rear end of the core; and
   (g) pivot means interconnecting the lever and the body portion whereby the lever is free to move between a locked position adjacent and an unlocked position away from the body position.

5. The handle of claim 4 wherein the channel is at 30° to the bore.

6. The handle of claim 4 wherein said bore has a substantially D-shaped cross-section defining a substantially flat side.

7. The handle of claim 6 wherein said channel communicates with the substantially flat side of the D-shaped bore.

* * * * *